(12) United States Patent
Gupta et al.

(10) Patent No.: US 8,575,313 B2
(45) Date of Patent: Nov. 5, 2013

(54) PROCESS FOR EXTRACTING KERATIN

(75) Inventors: Arun Gupta, Kuantan (MY); Ramanan Perumal, Kuantan (MY)

(73) Assignee: Universiti Malaysia Pahang (MY)

( * ) Notice: Subject to any disclaimer, the term of this patent is extended or adjusted under 35 U.S.C. 154(b) by 7 days.

(21) Appl. No.: 13/220,718

(22) Filed: Aug. 30, 2011

(65) Prior Publication Data
US 2012/0130048 A1 May 24, 2012

(30) Foreign Application Priority Data
Nov. 19, 2010 (MY) .................. 2010005452

(51) Int. Cl.
*A61K 38/17* (2006.01)

(52) U.S. Cl.
USPC ........................................ 530/357

(58) Field of Classification Search
USPC ........................................ 530/357
See application file for complete search history.

(56) References Cited

U.S. PATENT DOCUMENTS

| | | |
|---|---|---|
| 4,186,188 A | 1/1980 | Gumprecht |
| 5,395,613 A | 3/1995 | Holland |
| 6,858,215 B2 | 2/2005 | Buck |
| 7,220,405 B2 | 5/2007 | Huang et al. |
| 2006/0134092 A1 | 6/2006 | Miwa et al. |

FOREIGN PATENT DOCUMENTS

JP   2009298737 A   12/2009

OTHER PUBLICATIONS pH of KCN :: < http://www.highlands.edu/academics/divisions/scipe/chemistry/Site/GHandouts_files/Weak%20Acid-Base%20Equilibria.pdf > downloaded Nov. 1, 2012.*
Marshall et al., "High Sulphur Proteins from alpha-Keratins II.", Aust. J. Biol. Sci., 1976, 29:11-20.*
Wingfield, P., Protein Precipitation Using Ammonium Sulfate, Curr. Protocols in Protein Sci., May 2001, Supplement 13, Appendix 3F: A.3F1-A.3F.8.*
Tosik et al., "Biocomposites with a Content of Keratin from Chicken Feathers", Fibres & Textiles in Eastern Europe, Jan. / Mar. 2007, vol. 15, No. 1 (60).*

* cited by examiner

*Primary Examiner* — Suzanne M Noakes
(74) *Attorney, Agent, or Firm* — Galbreath Law Offices, P.C.; John A. Galbreath

(57) ABSTRACT

The present invention relates to a process for extracting keratin from poultry feather, and provides a quicker process thus allowing large-scale productions of the keratin production to be carried out in timely manner thus increasing the productivity and efficiency of such process.

7 Claims, No Drawings

PROCESS FOR EXTRACTING KERATIN

FIELD OF INVENTION

The present invention relates to a process for extracting keratin from poultry feather.

BACKGROUND OF INVENTION

Keratin has high value in cosmetics and medical industry. The keratin source usually used may be from several origins: may be derived from human hair fibers, wool, animal hair, feathers and horns.

Existing documents relating to keratin hydrolysates, and its use in cosmetics have been described in. U.S. Pat. No. 7,220,405. The patent describes a cosmetic formulation which has peptides base, like conditioners and hair dye creme lotion, body moisturizers, skin tone cream and nail enamels. Peptides have been described as being able to connect with high affinity to hair, skin and nails. Thus, this work aimed the development of personal care products containing peptides, from collagen, elastin, soybean, casein, silk among others, coupled directly or via a spacer to the product active agent.

U.S. Pat. No. 4,186,188 describes the use of trypsin to hydrolyse proteins in general, generating polypeptides from 200 to 2000 Da with positive charge that can be used in cosmetic formulations to hair, nails and skin.

US 2006/134092 and U.S. Pat. No. 5,395,613 describe peptidases (enzymatic characterization work) produced by microorganisms of the genus *Bacillus* and *Micrococcus sedentarius*, able to degrade proteins highly resistant to denaturation and degradation, including keratin, prion and collagen.

The above patents were aimed at describing a *Bacillus* or *Micrococcus sedentarius* peptidase towards the degradation of proteins that are difficult to degrade, like keratin.

U.S. Pat. No. 6,858,215 presents a method for the treatment of hyperkeratinized tissues in mammals using proteolytic enzymes originally developed for the hydrolysis of proteins associated with food and currently is commonly used to soften meat and improve the food taste. The composition of the product developed in this patent has softening enzymes, which soft and exfoliates skin hyperkeratinized formations, as callosities, granules, drying, scaly skin and keratosis without damaging the surrounding tissues by selective lysis of hyperkeratinized tissues. The enzymes used (1 to 15% in the formulation) were the subtilisin Carlsberg and a fungal peptidase of *Aspergillus oryzae*.

JP 2009298737 further disclosed a method for producing keratin from poultry feather. The feather is washed with a neutral detergent, rinsed with water and dried. The feather is mixed with 50 mL of a thioglycolic acid solution having 0.2 mol/L concentration adjusted to pH 11.0 with sodium hydroxide, stirred and shaken for 48 hours, the solution is adjusted to 30 C and adjusted to pH 7 with acetic acid. The solution is mixed with 50 mL of sodium bromate solution having 0.4 mol/L concentration by gradually adding the sodium bromate solution over 4 hours, then the solution is allowed to stand for 20 hours. Then insoluble matter is filtered off from the solution, the solution is adjusted to approximately pH 3.5 with acetic acid, a polymer substance is precipitated and the precipitate is recovered by centrifugal separation. The precipitate is made into a paste state acidic with acetic acid and preserved at a dark cold place.

The process suggested by the above prior art are tedious and time consuming. Hence, there is a need for an alternate process which is simpler thus avoiding the tediousness of the process disclosed in the prior art.

Additionally, there is a need for a quicker process thus allowing large-scale productions of the keratin production to be carried out in timely manner thus increasing the productivity and efficiency of such process.

SUMMARY OF INVENTION

It is a primary object of the invention to provide a process for extracting keratin from poultry feathers which avoids the drawbacks or disadvantages of the prior art.

It is also an object of the present invention to provide a process for extracting keratin from poultry feathers which is efficient and renders high productivity in large scale applications.

These and various other objects, features, advantages, and benefits of the present invention can be more fully appreciated with reference to the detailed description that follow.

DETAILED DESCRIPTION OF INVENTION

Persons of ordinary skill in the art can contemplate many alternatives, variations and modifications within the scope of the invention described herein.

In one preferred embodiment, the present invention provides an improved process for extracting keratin from poultry feathers.

The present method comprises the following steps,
a. Blending the feathers;
b. Dissolving the feathers in a basic solvent;
c. Filtering the composition and separating the composition to remove any solid particles thus collecting the supernatant liquid;
d. Adding ammonium sulphate to the supernatant liquid; and
e. separation to precipitate the resulting keratin.

The chicken feathers are collected, washed and soaked in ether to degrease it. Other effective alcohol solvents could also be used for this purpose. The feathers are then washed with soap, dried and subsequently blended into small pieces.

Next, the blended chicken is dissolved in KCN (potassium cyanide) and left for 4-6 hours. The solution is observed continuously from time to time to ensure the temperature of the solution is maintained at 30° C., and stirred occasionally using rod.

After 4-6 hours, the solution is filtered to remove all feather particles and centrifuged at 10,000 rpm for 5 min to remove tiny particles.

The supernatant liquid is then fitered using paper as a precaution so that no solid particle present in the solution.

Next, the supernatant liquid is placed in a magnetic stirrer and continuously stirred while ammonium sulphate solution is added drop wise. It is observed that the solution went through a color change. Once no further color change is observed, the addition of ammonium sulphate is stopped.

The solution is centrifuged at 10,000 rpm for 5 mins to obtain a precipitate. The precipitate obtained is carefully transferred to a beaker and mixed with deionized water.

To confirm the presence of protein, a burrette test is performed as follows;
1. 1% copper sulphate solution and 1% potassium hydroxide is prepared separately.
2. 1:1 mixture ratio of the collected precipitate to the potassium hydroxide solution is prepared.
3. Copper sulphate solutions are added dropwise to the mixture solution. The solution changed color to purple, indicating presence of protein in the precipitated solution.

Given the precipitated solution comprises deionized water and precipitation occurs, it is proved that the precipitate is protein.

4. The protein solution is further analyzed in FTIR to detect its composition and subsequently compare with standard amino acid concentration graphs.

Natural protein obtained from the invention is keratin and according to a most preferred embodiment of the invention, the keratin is derived from chicken feather. However, other poultry feather could also be used.

It is obvious to an ordinary person skilled in the art that the present invention could be modified with respect to techniques and additional chemicals employed while preserving the gist of the invention.

Keratin as such derived via the present invention could be used in cosmetic products such as shampoo, conditioner, moisturizer etc. Additionally keratin could also be used in deep cleansing masks, eye serums, anti-aging creams and body lotions, as well as in bone medical treatment.

It shall be obvious to an ordinary person skilled in the art with regard to the huge potential applications of keratin.

The invention claimed is:

1. A method for extracting keratin from poultry feathers comprising the following steps: (a) dissolving the feathers in a basic solvent; (b) filtering the resultant composition from step (a) to separate and remove any solid particles and collecting the supernatant liquid; (c) adding ammonium sulphate to the supernatant liquid to precipitate the keratin; and (d) separating the precipitated keratin; and wherein the feathers are dissolved in KCN prepared together with NaOH.

2. The method of claim 1, wherein the poultry feathers are chicken feathers.

3. The method of claim 1, wherein the feathers are broken into small pieces before the dissolving step.

4. The method of claim 1, wherein the feathers are dissolved in KCN solution and left to stand for 6 hours.

5. The method of claim 1, wherein the supernatant liquid is filtered using filter paper to ensure no solid particle is present in the solution.

6. The method of claim 1, wherein the ammonium sulphate solution is added dropwise to the feather filtrate solution until no further significant color change is observed in the solution.

7. The method of claim 1, wherein the filtrate solution is separated via centrifugation at 10000 rpm for 5 min to obtain a precipitate comprising the keratin.

* * * * *